(12) United States Patent
Deck

(10) Patent No.: US 10,744,067 B2
(45) Date of Patent: Aug. 18, 2020

(54) FILLING AID AND METHODS FOR SELF-FILLING A CARTRIDGE

(71) Applicant: Roche Diabetes Care, Inc., Indianapolis, IN (US)

(72) Inventor: Frank Deck, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 16/160,798

(22) Filed: Oct. 15, 2018

(65) Prior Publication Data
US 2019/0110953 A1    Apr. 18, 2019

(30) Foreign Application Priority Data
Oct. 17, 2017  (EP) ..................................... 17196804

(51) Int. Cl.
*A61J 1/20*     (2006.01)
*A61J 1/14*     (2006.01)
*A61M 5/178*    (2006.01)
*A61M 5/145*    (2006.01)

(52) U.S. Cl.
CPC ........... *A61J 1/2089* (2013.01); *A61J 1/1406* (2013.01); *A61J 1/20* (2013.01); *A61J 1/201* (2015.05); *A61J 1/2048* (2015.05); *A61J 1/2096* (2013.01); *A61M 5/14566* (2013.01); *A61M 5/1782* (2013.01); *A61J 2200/76* (2013.01)

(58) Field of Classification Search
CPC .. A61J 1/00; A61J 1/062; A61J 1/2089; A61J 1/2096; A61J 1/20; A61J 1/201; A61M 5/14566; B65B 3/003
See application file for complete search history.

(56) References Cited

U.S. PATENT DOCUMENTS

| 4,528,268 | A | * | 7/1985 | Andersen | ................ | C12Q 1/22 |
| | | | | | | 206/219 |
| 5,649,912 | A | | 7/1997 | Peterson | | |
| 2008/0215030 | A1 | * | 9/2008 | Ritsher | .................. | A61J 1/062 |
| | | | | | | 604/413 |
| 2008/0269713 | A1 | | 10/2008 | Kavazov | | |
| 2009/0082751 | A1 | * | 3/2009 | Reynolds | .............. | A61J 1/2089 |
| | | | | | | 604/413 |

(Continued)

FOREIGN PATENT DOCUMENTS

| EP | 0 143 895 A1 | 6/1985 |
| EP | 2 039 382 A1 | 3/2009 |
| EP | 2 510 914 A1 | 10/2012 |

(Continued)

*Primary Examiner* — Craig M Schneider
*Assistant Examiner* — Jason K Niesz
(74) *Attorney, Agent, or Firm* — Bose McKinney & Evans LLP

(57) ABSTRACT

A filling aid for self-filling a cartridge from a storage vessel is disclosed. The filling aid has a housing that receives a fillable cartridge. A stopper is provided that interacts with the housing and is configured to enter the cartridge and a cannula is provided that is configured to pierce a septum of the cartridge. The housing is movable from an initial position in which the stopper is maintained outside the cartridge to an activated position in which the stopper is inserted in the cartridge and the septum is pierced by the cannula. Methods of manufacturing and using the filling aid are also disclosed.

18 Claims, 5 Drawing Sheets

(56) References Cited

U.S. PATENT DOCUMENTS

2010/0276034 A1* 11/2010 Gonnelli ............... A61J 1/2089
141/18

FOREIGN PATENT DOCUMENTS

| EP | 2 510 963 A1 | 10/2012 |
|----|---|---|
| EP | 3 138 597 A1 | 3/2017 |
| WO | WO 03/090822 A1 | 11/2003 |
| WO | WO 2009/142944 A1 | 11/2009 |

* cited by examiner

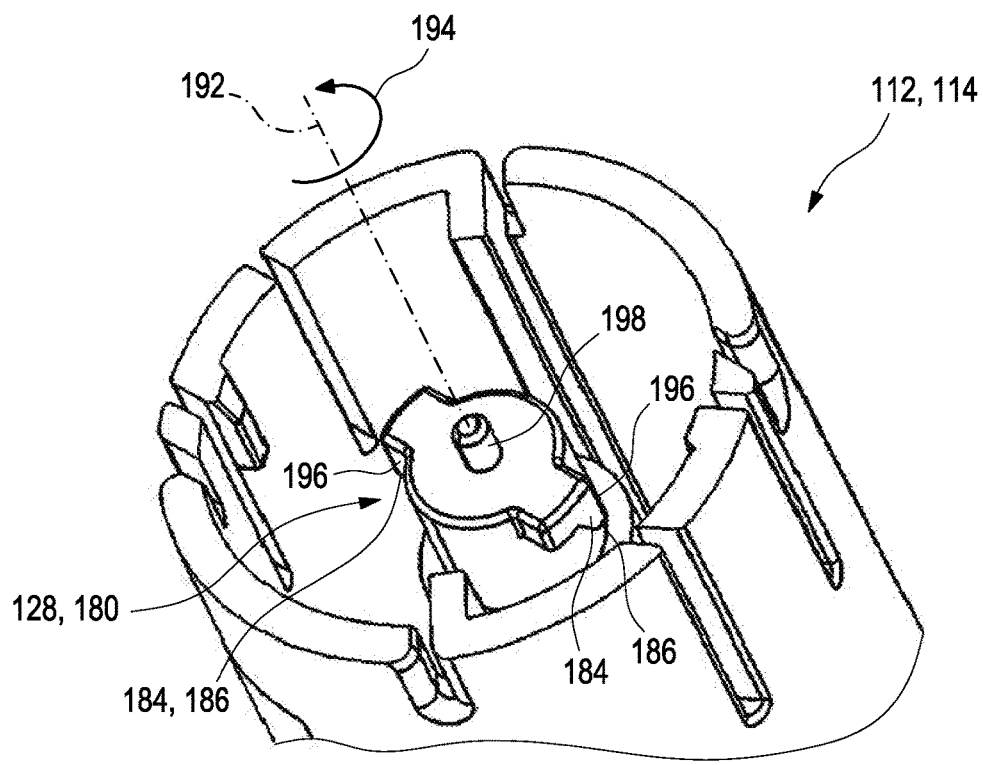
Fig. 6 A
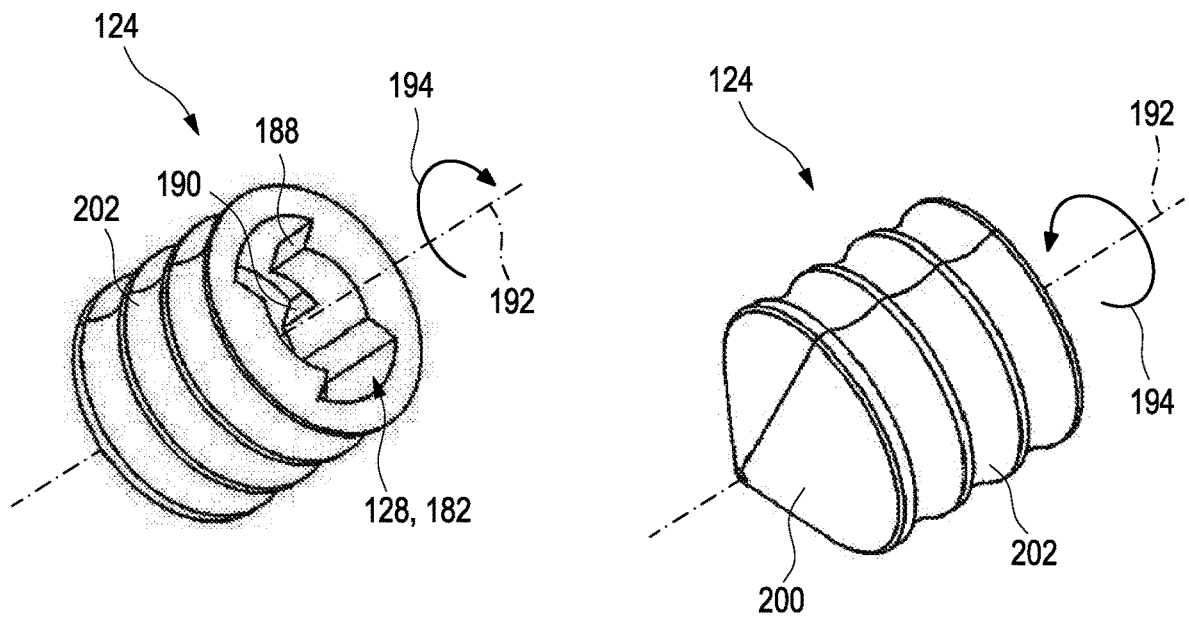
Fig. 6 B
Fig. 6 C

FILLING AID AND METHODS FOR SELF-FILLING A CARTRIDGE

RELATED APPLICATIONS

This application claims priority to EP 17 196 804.3, filed on Oct. 17, 2017, the entire disclosure of which is hereby incorporated herein by reference.

BACKGROUND

This disclosure relates to the field of preparing cartridges for ambulatory infusion systems. Particularly, this disclosure relates to a filling aid for self-filling a cartridge from a storage vessel, a kit with such a filling aid and a use of the filling aid. This disclosure further relates to methods of manufacturing both a filling aid and a kit, and a method of using a filling aid for self-filling a cartridge. The filling aid, the kit and the methods according to this disclosure may mainly be used for self-filling a cartridge, usable with ambulatory infusion pumps, specifically with medication pumps. Medication pumps are widely used for administrating liquid medications, such as insulin. Thus, this disclosure may be used for insulin delivery. This disclosure may both be applied in the field of home care as well as in the field of professional care, such as in hospitals. Other applications are feasible.

Ambulatory infusion pumps, such as medication pumps, are widely used in medical therapy. A cartridge containing the liquid medication is applied to the medication pump. For that purpose, the cartridge previously has to be filled with the medication. In EP 2 510 914 A1 a connector device for fluidly connecting two septum sealed containers is disclosed, which may be used for filling a cartridge. EP 2 510 914 A1 discloses a connector device for fluidly connecting two septum sealed containers. The connector device comprises a first member and a second member that are slidably displaceable in regard to each other along an axis between a first and a second position. The first member comprises a hollow transfer needle with two pointed ends, arranged parallel to said axis in such a way that a septum of a first one of the containers is penetrated by one end of the needle when said first container is introduced into a receptacle of the first member. The second member comprises means for releasably coupling to the second one of the two containers. The other end of the needle does not come into contact with a septum of the second container coupled to the second member when the members are in the first position. The other needle end penetrates the septum of the second container when the members are in the second position, thereby establishing a fluid connection between the two containers. The first member comprises means for releasably coupling to the second container coupled to the second member, wherein said coupling means of the first member can be coupled to said second container when the two members are in the second position, and cannot couple to said second container when the two members are in the first position.

Examples of sealing a cartridge during filling of the cartridge are known from EP 2 039 382 A1 and EP 3 138 597 A1. EP 2 039 382 A1 discloses an ampoule for a flowable substance comprising an ampoule body with an interior space for receiving the flowable substance and with an inner casing surface. The ampoule comprises a plunger comprising at least one sealing element which is arranged in the interior space so that it can be displaced along a displacement direction (R), wherein the sealing element is in contact with the inner casing surface in a contact zone (K) along the outer circumference of the at least one sealing element. The inner casing surface has a guide region and a sealing region along the displacement direction (R) where the cross-section of the interior space in a plane at right angles to the displacement direction (R) in the guide region is designed such that the at least one sealing element has a first compression state when the contact zone (K) is situated in the guide region. The sealing region is designed such that the at least one sealing element has a second compression state when the contact zone (K) is situated in the sealing region. The inner casing surface together with the at least one sealing element forms a fluidic seal when the at least one sealing element is in the second compression state. The ampoule further comprises a second locking device which prevents the contact zone (K) from moving out of the sealing region into the guide region against the displacement direction (R).

EP 3 138 597 A1 discloses a dosing unit for use in an ambulatory infusion system, the dosing unit including: a dosing cylinder and a piston, the piston being arranged inside the dosing cylinder and in a sliding displaceable manner along a displacement axis (A). The piston is convertible from a storing configuration into an operational configuration, wherein a circumferential sealing member of the piston is mechanically relieved in the storing configuration and is in sealing and sliding engagement with a circumferential inner surface of the dosing cylinder in the operational configuration. The dosing unit includes a configuration switch member in operative mechanical coupling with the piston, the configuration switch member being movable relative to the piston from a storing position into an operational position, thereby switching the piston configuration from the storing configuration to the operational configuration.

In many circumstances it is desirable to enable users without professional training to carry out a filling of the cartridge. Especially in the field of diabetes therapy, where a user might carry an insulin infusion pump device continuously night and day, it is desirable to enable the user without professional training to carry out a filling of the cartridge without assistance from professionally trained medical staff. Such an infusion pump device is, for example, known from EP 0 143 895 A1. In order to enable a user without professional training to carry out a filling of the cartridge without assistance, an easy, quick, inexpensive and safe filling device is desirable.

SUMMARY

This disclosure teaches a filling aid which addresses the above-mentioned technical challenges, specifically, a filling aid for self-filling a cartridge.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Still further it shall be understood for purposes of this disclosure and appended claims that, regardless of whether the phrases "one or more" or "at least one" precede an element or feature appearing in this disclosure or claims, such element or feature shall not receive a singular interpretation unless it is made explicit herein. By way of non-limiting example, the terms "cartridge," "cannula," "stopper," to name just a few, should be interpreted wherever they appear in this disclosure and claims to mean "at least one" or "one or more" regardless of whether they are introduced with the expressions "at least one" or "one or more." All other terms used herein should be similarly interpreted unless it is made explicit that a singular interpretation is intended.

Further, as used in the following, the terms "preferably," "more preferably," "particularly," "more particularly," "specifically," "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect of this disclosure, a filling aid for self-filling at least one cartridge from a storage vessel is disclosed. The filling aid comprises at least one housing configured for receiving the cartridge, at least one stopper interacting with the housing and configured for entering the cartridge, and at least one cannula configured for piercing a septum of the cartridge. The housing is configured to be activated such that the stopper is maintained outside the cartridge prior to activation. The housing further is configured to be activated such that the stopper is inserted into the cartridge and the septum is pierced by the cannula, upon activation.

The term "filling aid" as used herein is a broad term and is to be given its ordinary and customary meaning to a person of ordinary skill in the art and is not to be limited to a special or customized meaning. The term specifically may refer, without limitation, to an arbitrary device configured for assisting a user in self-filling a cartridge from a storage vessel.

The term "self-filling" as used herein is a broad term and is to be given its ordinary and customary meaning to a person of ordinary skill in the art and is not to be limited to a special or customized meaning. The term specifically may refer, without limitation, to a process of filling an arbitrary device, for example the cartridge, with a fluid, wherein the process of filling is carried out by a user, e.g., a patient, himself or herself. Specifically the user may be an ordinary person, for example the user may be a person without professional training in the medical field.

The term "cartridge" as used herein is a broad term and is to be given its ordinary and customary meaning to a person of ordinary skill in the art and is not to be limited to a special or customized meaning. The term specifically may refer, without limitation, to an arbitrary device configured for receiving and/or storing and/or delivering a fluid. The cartridge may have a cylindrical shape. For example, the cartridge may have a roller shape. Specifically, the cartridge may have a bottle shape. The cartridge may be made from a clear material; specifically, the cartridge may be made from a transparent and/or translucent material. The cartridge may further be made from an airtight material. For example, the cartridge may be made from glass and/or polymer. The cartridge may have at least two openings; for example, the two openings can be arranged on opposing sides of the cartridge. Specifically the cartridge may have a bottle shape with openings at the bottle opening and at the base of the bottle. At least one of the openings of the cartridge may be covered by a septum.

The term "septum" as used herein is a broad term and is to be given its ordinary and customary meaning to a person of ordinary skill in the art and is not to be limited to a special or customized meaning. The term specifically may refer, without limitation, to an arbitrary sealing element configured for sealing a container and providing an environmental protection for the content of the container against moisture and/or an ambient atmosphere, or the like. As an example, the septum may be or may comprise at least one pierceable foil, disk, shim, plug or plate, made of a material which may be pierced by a cannula and which may re-seal a piercing hole generated by the cannula after retraction of the cannula. Specifically, the septum may be made of an elastic material such as an elastomer. The septum may be penetrable by an elongate object with a small diameter such as by the cannula. After a penetration by the elongate object, an opening of the septum caused by the elongate object may be closed by itself and the septum may further be configured to provide a tight sealing of the container from the environment. Specifically, the septum may be configured for sealing at least one opening of the cartridge.

The term "cannula" as used herein is a broad term and is to be given its ordinary and customary meaning to a person of ordinary skill in the art and is not to be limited to a special or customized meaning. The term specifically may refer, without limitation, to an arbitrary element which may be or may comprise a hollow tube or a hollow needle. The cannula may comprise a round profile; for example, the profile may have the shape of an O. Other shapes of the profile are also feasible. For example, the profile may change over the length of the cannula. The cannula may have two opposing ends. The two opposing ends may each have a sharp. The two opposing ends may comprise a beveled tip shape, configured for facilitating a piercing of a surface. The cannula may particularly be configured to establish a fluid connection between the two opposing ends of the cannula.

The term "storage vessel" as used herein is a broad term and is to be given its ordinary and customary meaning to a person of ordinary skill in the art and is not to be limited to a special or customized meaning. The term specifically may refer, without limitation, to an arbitrary device, e.g., a container, configured for storing and/or delivering a fluid. The storage vessel may comprise at least one opening. The at least one opening of the storage vessel may be sealed by a seal. The seal may be configured for providing an environmental protection for the content of the storage vessel against moisture and/or an ambient atmosphere, or the like. The storage vessel may be made from a clear material; specifically, the storage vessel may be made from a transparent and/or translucent material. For example, the storage vessel may be made from glass and/or polymer. The storage vessel may further have a bottle shape, such that the opening of the storage vessel is positioned at one end of a bottleneck, merging into an arbitrary shaped body of the storage vessel. Specifically the storage vessel may contain a fluid, such as a fluid medication.

The term "stopper" as used herein is a broad term and is to be given its ordinary and customary meaning to a person of ordinary skill in the art and is not to be limited to a special or customized meaning. The term specifically may refer, without limitation, to an arbitrary device configured to moving in a predefined trajectory and converting the movement into a pressure and vice versa. Specifically, the stopper may be configured to seal an opening of a container and, by advancing inside the container, applying the pressure onto a fluid contained inside the container. For example, the stopper may be and/or comprise a movable sealing element arranged inside the cartridge. The stopper may be at least partially made from an elastomeric material. The stopper may further have a cylindrical and/or conical shape. Specifically, the stopper may comprise a first part having a conical shape merging into a second part having a cylindrical shape. The second part may have a cylindrical shape with varying diameters. The varying diameters may be arranged such that the shell surface of the cylindrically shaped second part may have a wavelike surface structure. The shell surface of the cylindrically shaped second part may be configured such as to reduce friction between the shell surface of the stopper and an inner surface of the container. In particular, the stopper may be at least partially made from flexible material. For example, one or more of an elastomeric polymer, a rubber or a silicone may be used. Specifically, as an example, bromobutyl rubber and thermoplastic elastomers can be named as possible materials of the stopper. The thermoplastic elastomers may, in particular, be processed in an injection molding process. Hence, the stopper may be made from a single-phase thermoplastic elastomer. However, the thermoplastic elastomers may also, for example, be processed in a multi-component injection molding process, particularly in a two-component injection molding process, allowing the processing of a single part, e.g., the stopper, comprising more than one material, specifically, more than one thermoplastic elastomer, combining the properties of the materials into the one part. Specifically, as an example, the two-component injection molding process may enable a manufacturing of a stopper, comprising a hard body equipped with a soft sealing surface structure. Thereby, the advantages, such as a mechanical stability of the hard body functioning as a form-generating element may be combined with the advantages, such as a sealing property, of the soft surface structure functioning as a form-adaptive element into one stopper. However, a one-piece manufacturing of the stopper using only one component may also be feasible.

The term "housing" as used herein is a broad term and is to be given its ordinary and customary meaning to a person of ordinary skill in the art and is not to be limited to a special or customized meaning. The term specifically may refer, without limitation, to an arbitrary element configured to provide mechanical support and/or mechanical protection for other elements, such as the stopper and/or the cartridge and/or the cannula. Specifically, the housing may be configured to restrict spatial movement and/or positioning of the other elements. The housing specifically may be at least partially closed and may fully or partially surround all or some of the other components of the filling aid. The housing, as an example, may be made fully or partially of at least one plastic material and/or metal. More specifically, the housing may be configured to be activated.

The term "to be activated" as used herein is a broad term and is to be given its ordinary and customary meaning to a person of ordinary skill in the art and is not to be limited to a special or customized meaning. The term specifically may refer, without limitation, to a process indicating a development from a disengaged and/or deactivated state to an engaged and/or activated state. For example, a composition of elements may be activated by physically changing spatial arrangements of the elements, such that an interaction between the elements may be altered. Specifically, the housing may be activated by physically changing the spatial arrangement of adjoining elements, e.g., the stopper and/or the cartridge and/or the cannula. The activated housing may, for example, allow an interaction between at least two adjoining elements, wherein such an interaction may not be allowed and/or possible in a deactivated state of the housing.

The housing may be configured such that the septum of the cartridge is pierced by the cannula while advancing the stopper inside the cartridge. Specifically, piercing the septum by the cannula and advancing the stopper inside the cartridge may be performed in an overlapping fashion. For example, advancing the stopper inside the cartridge may not be concluded when the septum of the cartridge is pierced by the cannula or vice versa.

The housing may further be configured to be activated in a multiple-step activation. Thus, the activation may comprise multiple activations or activation steps, which, as an example, may be performed sequentially. A first activation may comprise the inserting of the stopper into the cartridge. A second activation may comprise the piercing of the septum by the cannula.

Prior to activation of the housing, a first gap may exist between the stopper and the cartridge. Preferably the gap between the stopper and the cartridge may be arranged such that no physical contact exists between the stopper and the cartridge prior to activation of the housing. Further, a second gap may exist between the cannula and the septum prior to activation of the housing. Preferably, the gap between the cannula and septum may be arranged such that, prior to activation of the housing, no physical contact exists between the cannula and the septum.

The housing may comprise at least one fill level indicator for indicating a filling level of the cartridge. The fill level indicator may indicate the filling level of the cartridge by means of providing a fill level indicator marking, such as, for example, a scale. The fill level indicator may further comprise a fill level identifier, such as, for example, a marker and/or a vision panel, configured to allow a visual identification of the filling level.

The housing may further comprise at least two housing parts and at least one guiding device. By means of the guiding device, the at least two housing parts may be movable with respect to each other. The movement of the at least two housing parts with respect to each other may activate the housing. The activation of the housing may initiate the filling of the cartridge. Specifically, the movement of the at least two housing parts with respect to each other by means of the guiding device may arrange the stopper and/or the cartridge and/or the cannula in such a way that a filling of the cartridge may be initiated. Preferably the movement of the at least two housing parts may activate the housing such that an interaction between the stopper and/or the cartridge and/or the cannula may be allowed.

The term "guiding device" (also referred to herein as "guide") as used herein is a broad term and is to be given its ordinary and customary meaning to a person of ordinary skill in the art and is not to be limited to a special or customized meaning. The term specifically may refer, without limitation, to an arbitrary device configured for guiding a spatial movement of at least one element relative to another element. The guiding device may preferably comprise two separate parts. One of the parts may be configured for providing a trajectory, specifically by comprising means for defining a direction of movement, such as, for example, by comprising a groove and/or a slot. Another one of the parts may provide the means to follow the trajectory, such as, for example, a guiding protrusion running in the groove or the slot, wherein the guiding protrusion may have a shape customized for following the trajectory. Specifically, the shape of the guiding protrusion may form a negative of a profile of the groove and/or the slot.

One of the housing parts may comprise a handle piece. Furthermore, the handle piece and the stopper may be connected by means of a coupling. The coupling may comprise a bayonet joint, configured for establishing a releasable mechanical connection between the stopper and the handle piece. However, additionally or alternatively, the coupling may comprise screw threads, specifically multistart threads, for establishing a releasable mechanical connection between the stopper and the handle piece. In particular, the coupling may comprise two interacting threads, more particularly, two complementary threads configured for interacting with one another forming a threaded coupling, such as a male and a female thread interacting with each other. Thus, one of the parts of the coupling, either the handle piece or the stopper, may comprise the male thread, specifically an external thread, configured to interact with the female thread. Hence, the respective other part of the coupling may comprise the female thread, specifically an internal thread. As an example, the handle piece may comprise the male thread and the stopper may comprise the female thread. Thus, allowing the releasable mechanical connection between the stopper and the handle piece to be established by screwing the handle piece in the stopper, specifically by turning the handle piece and the stopper around an axis, particularly around a thread axis, in a contra-rotating fashion. The rotational movement or tilting, as an example, may take place about a tilting angle, from an initial angle to a final angle, wherein, in the position of the final angle, as an example, the stopper is locked to the handle piece. The tilting angle, for example, may be an angle in the range of 10° to 360°, such as an angle of 20° to 270°, preferably an angle of 30° to 180°, more preferably an angle of 100°.

The term "bayonet joint" as used herein is a broad term and is to be given its ordinary and customary meaning to a person of ordinary skill in the art and is not to be limited to a special or customized meaning. The term specifically may refer, without limitation, to an arbitrary connector or connection between two bayonet contours in a bayonet fashion. The bayonet joint may be formed by two bayonet contours. A stopper bayonet contour and a handle piece bayonet contour, in conjunction, may form the bayonet joint. The term "bayonet contour" as used herein is a broad term and is to be given its ordinary and customary meaning to a person of ordinary skill in the art and is not to be limited to a special or customized meaning. The term specifically may refer, without limitation, to a component or part of an element which is configured to interact with a counterpart bayonet contour in order to form a bayonet joint or a bayonet connection. Thus, the stopper bayonet contour and the handle piece bayonet contour may be complementary bayonet contours configured for performing a bayonet connection or, in conjunction, a bayonet joint. Therein, one of the two bayonet contours, either the stopper bayonet contour or the handle piece bayonet contour, may be or may comprise a male bayonet contour, such as a male bayonet plug. The respective other one of the two bayonet contours, either the stopper bayonet contour or the handle piece bayonet contour, may be or may comprise a female bayonet contour, such as a female bayonet plug. Therein, generally, one or both of the bayonet contours involved may comprise at least one protrusion and, in a complementary fashion, the other one of the bayonet contours may comprise at least one bayonet groove or bayonet slot in which the protrusion may be guided.

The bayonet groove or bayonet slot generally may comprise at least two different sections. In a first section, the protrusion may simply be moved in an axial fashion, with respect to an axis which interconnects the two bayonet contours. Thus, as an example, while the protrusion is guided in the first section, the two components which will be interconnected by the bayonet joint simply may be pushed together along the axis. In a second section, which directly or indirectly may follow the first section, the protrusion may be guided in a spiral or screwlike fashion around the axis. The bayonet groove or bayonet slot may comprise one or more further sections, such as one or more sections before the first section, one or more intermediate sections in between the first section and the second section and/or one or more sections behind the second section. Combinations of the named sections are feasible. Thus, as an example, the interconnection of the stopper and the handle piece may be formed by a sequence of movements or relative movements of these two components, such as a first linear movement along the axis and, subsequently, a rotational movement. Thus, generally, the establishing of the releasable mechanical connection by using the bayonet joint may imply a combination of an axial movement and a rotational movement, in a subsequent fashion, with preferably the axial movement preceding the rotational movement. The rotational movement, as an example may imply pivoting the handle piece with respect to the stopper or vice versa, about the axis. The axis, as an example, may be a rotational axis of the bayonet contour, such as an axis of symmetry of the bayonet joint. The axis, as an example, may be parallel to the first direction of the movement of the at least two housing parts by means of the guiding device when activating the housing. The rotational movement or tilting, as an example, may take place about a tilting angle, from an initial angle to a final angle, wherein, in the position of the final angle, as an example, the stopper is locked to the handle piece. The tilting angle, for example, may be an angle in the range of 10° to 130°, such as an angle of 20° to 110°, preferably an angle of 25° to 90°, more preferably an angle of 30°.

When releasing the bayonet joint, the movements may be performed in the opposite order. Thus, as an example, the rotational movement may be reversibly performed, specifically when releasing the bayonet joint the tilting may be performed in the opposite direction than when closing the bayonet joint. For example, the handle piece may, in order to release the bayonet joint, be rotated counterclockwise with respect to the stopper, if the bayonet connection between the stopper and the handle piece had been established by rotating the handle piece clockwise with respect to the stopper. Subsequent to the tilting, a linear movement along the axis may be performed, such as to separate the stopper and the handle piece.

The bayonet joint may comprise at least one undercut. The undercut may be a part of the male bayonet contour. The term "undercut" as used herein is a broad term and is to be given its ordinary and customary meaning to a person of ordinary skill in the art and is not to be limited to a special or customized meaning. The term specifically may refer, without limitation, to an arbitrary convexity arranged at a surface of the male bayonet contour. Specifically the undercut may be and/or may comprise a protrusion, such as, for example, a protrusion having a pencil shaped form, a tooth shaped form or a jagged form. The undercut may be configured to increase a transmissible tensile force of the bayonet joint, for example the transmissible tensile force between the stopper and the handle piece. A tensile force between the stopper and the handle piece may be transmitted via a form closure by way of the bayonet joint. The transmissible tensile force of the bayonet joint may depend on the arrangement of the form closure. The undercut may establish a different arrangement of the form closure, such as to increase the transmissible tensile force, compared to the arrangement of the form closure without the undercut.

That bayonet joint may further comprise at least one centering pin. The centering pin may be configured to restrict a relative movement of the stopper and the handle piece. The term "centering pin" as used herein is a broad term and is to be given its ordinary and customary meaning to a person of ordinary skill in the art and is not to be limited to a special or customized meaning. The term specifically may refer, without limitation, to an arbitrary pin, such as, for example, a cone, peg or spike, arranged in a center of an element, wherein the center may be located on an axis of said element, such as a rotation and/or symmetry axis. Preferably the centering pin may be arranged on the rotation axis of the bayonet joint, e.g., on the rotation axis of the stopper and/or on the rotation axis of the handle piece. Specifically the centering pin may be configured to restrict a movement of the stopper with respect to the handle piece, such as a tilting of the stopper relative to the handle piece, or vice versa, prior to the activation of the housing. The centering pin may be configured to restrict the movement of the stopper or the handle piece by increasing friction between the stopper and the handle piece. The centering pin may specifically be configured for securing an axial alignment between an axis of the stopper and an axis of the handle piece. Particularly, in the deactivated state of the housing the stopper may be secured axially by the centering pin, ensuring the stopper remains in position. Thus, the centering pin may be configured to prevent external forces, possibly occurring during storage and/or transportation, from affecting the axial position of the stopper. Specifically, the centering pin may be configured to prevent the stopper from closing the gap between the stopper and the cartridge prior to the activation of the housing. However, in order to minimize an interference of the friction caused by the centering pin between the stopper and the handle piece in an activated state of the housing, a diameter d of the centering pin may be chosen to be as small as possible, such as $0 < d \leq 3$ mm.

The handle piece may comprise at least one handling recess. The handling recess may be configured to define a force transmission area for transmission of a force onto the handling piece. The handling recess may comprise at least one opening. Preferably, the handling piece may comprise a plurality of openings. The opening may have a round and/or an angular shape. Specifically the opening may have an oval shape. Other shapes of the opening are also feasible.

The handle piece may further comprise at least a first part of the guiding device. Thus, the handle piece may either comprise a part of the guiding device configured for providing the trajectory, or the handle piece may comprise a part of the guiding device configured to follow the trajectory.

The handle piece may further comprise at least a first part of the fill level indicator. Thus, the handle piece may comprise the fill level indicator marking and/or the fill level identifier.

One of the housing parts may comprise a connection piece. The connection piece may be connected to the cannula. The cannula may be arranged inside the connection piece.

The connection piece may comprise at least a second part of the guiding device. Thus, the connection piece may comprise a second part of the guiding device, configured to form the guiding device in conjunction with the first part of the guiding device comprised by the handle piece.

The connection piece may further comprise at least a second part of the fill level indicator. Thus, the connection piece may comprise the fill level indicator marking and/or the fill level identifier. The fill level indicator may be formed, in conjunction, by the first part of the fill level indicator, comprised by the handle piece, and the second part of the fill level indicator, comprised by the connection piece.

The connection piece may further comprise at least one finger grip recess. The finger grip recess may be configured for defining a force transmission point. Thus, the finger grip recess may be configured to provide a defined space for the user to place at least one finger.

The connection piece may further comprise at least one cartridge receptacle. The cartridge receptacle may be configured to receive the cartridge. Preferably, the cartridge receptacle may be configured to releasably receive the cartridge, e.g., establish a releasable connection to the cartridge.

The connection piece may further comprise at least one storage vessel receptacle configured to receive the storage vessel. Preferably, the storage vessel receptacle may be configured to releasably receive the storage vessel, e.g., establish a releasable connection to the storage vessel.

The cannula may be configured to pierce the seal of the storage vessel. The cannula may further be configured to allow a transfer of a fluid between the storage vessel and the cartridge. The cannula may comprise two opposing ends. The two opposing ends of the cannula may each have a sharp. A first end of the cannula may be configured for piercing the septum of the cartridge. A second end of the cannula may be configured for piercing the seal of the storage vessel.

The guiding device may further be configured to determine a relative positioning of at least two parts of the filling aid. Particularly, the guiding device may be configured to determine the relative positioning of the at least two parts of the housing, such as the positioning of the handle piece relative to the positioning of the connection piece. Thus, the guiding device may further be configured to determine the relative positioning of the stopper and the connection piece, such as to restrict the movement of the stopper inside the cartridge. Preferably, the guiding device may be configured to restrict the movement of the stopper inside the cartridge, such as to prevent the stopper from being pulled out from inside the cartridge. Thus, the restricted movement of the stopper may prevent a leakage of the fluid.

The guiding device may specifically comprise means for defining a direction of movement, such as back moving locks or non-return devices, configured to restrict a backwards movement. Specifically, when activating the housing by moving the at least two housing parts by means of the guiding device, the defined direction of movement may prevent a separation of the housing parts by a movement in the opposite direction, e.g., a backwards movement. Hence, once the stopper is inserted into the cartridge and the septum is pierced by the cannula, a separation or disengagement of the at least two housing parts may only be possible by following the direction of movement defined by the guiding device. Particularly, a deactivation of the housing may only be possible by moving the housing parts by means of the guiding device, following a sequence of axial and/or rotational movements predefined by the guiding device to terminate the filling of the cartridge.

The housing may further comprise at least two abutments. The cartridge may be receivable in the housing, such that the cartridge may be fixed between the two abutments.

In a second aspect of the present disclosure, a kit for self-filling at least one cartridge from a storage vessel is disclosed. The kit comprises at least one filling aid, such as the filling aid described in the text above. The kit further comprises at least one cartridge for receiving a fluid, which can be received within the filling aid. The cartridge has at least one first opening covered by a septum. The cartridge has at least a second opening through which the stopper of the filling aid is insertable into the cartridge.

The kit may further comprise at least one storage vessel, wherein the storage vessel may be filled with at least one fluid.

In a third aspect of this disclosure, a use of the filling aid for self-filling a cartridge is disclosed. The use of the filling aid refers to a filling aid for self-filling a cartridge for insulin delivery. Specifically, the use of the filling aid refers to a filling aid for self-filling a cartridge for use with a medication pump.

In a fourth aspect of this disclosure, a method of manufacturing a filling aid for self-fillable cartridges is disclosed. The method of manufacturing a filling aid for self-fillable cartridges comprises the method steps as given in the independent claims and as listed below. The method steps may be performed in the given order. However, other orders of the method steps are feasible. Further, one or more of the method steps may be performed in parallel and/or in an overlapping fashion. Further, one or more of the method steps may be performed repeatedly. Further, additional method steps may be present which are not listed.

The method of manufacturing a filling aid for self-fillable cartridges comprises the following steps:
i) providing at least one housing for receiving the cartridge;
ii) providing at least one stopper, wherein the stopper interacts with the housing, wherein the stopper is configured for entering the cartridge;
iii) providing at least one cannula, wherein the cannula is configured for piercing a septum of the cartridge; and
iv) maintaining the stopper outside of the cartridge, wherein the stopper is arranged such that, upon activation of the housing, the stopper can be inserted into the cartridge.

The method of manufacturing a filling aid for self-fillable cartridges may further comprise the following steps:
v) positioning the filling aid inside a permeable foil; and
vi) sterilizing the filling aid in a sterilization process.

The positioning of the filling aid inside the permeable foil may specifically be necessary when sterilizing gas, particularly steam and/or ethylene oxide, is used in the sterilization process. However, other sterilization processes may be feasible, such as sterilization processes not requiring permeable foils. Specifically, sterilization processes that do not require the filling aid being positioned inside the permeable foil, such as for example radiation sterilization. Thus, step vi) sterilizing the filling aid in a sterilization process may be performed independent from a performing of step v) positioning the filling aid inside a permeable foil. Hence, generally, the sterilization may be performed without the filling aid being positioned inside the permeable foil.

Specifically, the method of manufacturing a filling aid for self-fillable cartridges may comprise manufacturing the filling aid as described above or as will further be described below.

In a fifth aspect of the present disclosure, a method of manufacturing a kit for self-fillable cartridges is disclosed. The method of manufacturing a kit for self-fillable cartridges comprises the method steps as given in the independent claims and as listed as follows. The method steps may be performed in the given order. However, other orders of the method steps are feasible. Further, one or more of the method steps may be performed in parallel and/or in an overlapping fashion. Further, one or more of the method steps may be performed repeatedly. Further additional method steps may be present which are not listed.

The method of manufacturing a kit for self-fillable cartridges comprises the following steps:
I) providing at least one cartridge for receiving a fluid;
II) providing at least one housing for receiving the cartridge;
III) providing at least one stopper, wherein stopper interacts with the housing, wherein the stopper is configured for entering the cartridge;
IV) providing at least one cannula, wherein the cannula is configured for piercing a septum of the cartridge; and
V) maintaining the stopper outside of the cartridge, wherein the stopper is arranged such that, upon activation of the housing, the stopper can be inserted into the cartridge;

The method of manufacturing a kit for self-fillable cartridges may further comprise the following steps:
VI) positioning the filling aid inside a permeable foil; and
VII) sterilizing the filling aid in a sterilization process.

The method of manufacturing a kit for self-fillable cartridges may further comprise providing a storage vessel filled with at least one fluid.

Specifically, the method of manufacturing a kit for self-fillable cartridges may comprise manufacturing the kit as described above or as will further be described below.

In a sixth aspect of the present disclosure, a method of using a filling aid for self-filling at least one cartridge from a storage vessel is disclosed. The methods of using a filling aid for self-filling at least one cartridge from a storage vessel comprises the method steps as given in the independent claims and as listed below. The method steps may be performed in the given order. However, other orders of the method steps are feasible. Further, one or more of the method steps may be performed in parallel and/or in an overlapping fashion. Further, one or more of the method steps may be performed repeatedly. Further, additional method steps may be present which are not listed.

The method of using a filling aid for self-filling at least one cartridge from a storage vessel comprises the following steps:

a) providing at least one housing for receiving the cartridge;
b) providing at least one stopper, wherein the stopper interacts with the housing, wherein the stopper is configured for entering the cartridge;
c) providing at least one cannula, wherein the cannula is configured for piercing a septum of the cartridge;
d) maintaining the stopper outside of the cartridge, wherein the stopper is arranged such that, upon activation of the housing, the stopper can be inserted into the cartridge; and
e) activating the housing, wherein the stopper is inserted into the cartridge and the septum is pierced by the cannula.

The method of using a filling aid for self-filling at least one cartridge from a storage vessel may further comprise maintaining the cannula outside of the septum prior to the activation of the housing.

Specifically, step e), activating the housing, of the method of using a filling aid for self-filling at least one cartridge from a storage vessel may further comprise the following substeps:
e1) advancing the stopper inside the cartridge;
e2) mating the filling aid and a storage vessel;
e3) piercing a seal of the storage vessel; and
e4) transferring at least one fluid between the storage vessel and the cartridge through the cannula.

The substep of piercing the septum by the cannula in step e), activating the housing, may be performed while performing step e1) advancing the stopper inside the cartridge.

Specifically, the method of using a filling aid may comprise using the filling aid as described above or as will be further be described below.

The devices and methods according to this disclosure may provide a large number of advantages over known methods and devices for self-filling cartridges. Thus, specifically, the disclosed filling aid and the kit may be suitable for performing a self-filling of a cartridge after longer storage periods than devices known in the art. The individual parts of the filling aid and/or the kit may be integrated in a storage-friendly, tension-free position, thereby minimizing the occurrence of plastic deformation during storage periods. Thus, for example, a full elastic restoring force may be available when self-filling the cartridge for functioning purposes. This may avoid possibly occurring adhesions between the stopper and the cartridge during the storage period. More specifically, adhesions leading to adhesive residues may be avoided. Particularly, the integration of the parts, more particularly the integration of the stopper and the septum of the cartridge within the filling aid or the kit, in a tension-free position may allow use of more cost-effective materials. Specifically the materials used for the stopper and the septum may be less expensive than conventional materials used by devices known in the art.

Furthermore, the devices and methods suggested in this disclosure may simplify a sterilization process prior to use of the devices and methods for self-filling cartridges compared to sterilization processes applied to methods and devices known from the art. Specifically, the existing gap between the cartridge and the stopper in a deactivated state of the housing may allow a usage of a sterilization gas, such as for example ethylene oxide, for sterilizing the disclosed devices. More specifically, the sterilization gas may be able to enter the cartridge through the gap between the stopper and the cartridge, sterilizing the inside of the cartridge. Subsequently, the sterilization gas may be able to leave the inside of the cartridge again through the gap between the stopper and the cartridge.

The disclosed devices and methods for self-filling cartridges may reduce the risk of leakage during self-filling the cartridge compared to methods and devices for self-filling cartridges known from the art. Specifically, maintaining the cannula outside of the septum of the cartridge prior to activation of the housing may reduce the risk of leakage during a filling of the cartridge. Particularly, an elasticity of the septum may be maintained by maintaining the cannula outside of the septum prior to activation. Thus, the elasticity, specifically an elastic property, of the septum may not be subjected to an accelerated aging process by being constantly pierced by the cannula prior to the filling of the cartridge. Hence, maintaining the cannula outside of the septum prior to activation of the housing may ensure an availability of a maximum elasticity, e.g., a full elastic property, of the septum during the filling of the cartridge. Specifically, the full elasticity of the septum may be available for sealing the cartridge, thereby preventing leakage of the cartridge, specifically preventing leakage between cannula and septum.

Further, the disclosed devices and methods for self-filling cartridges may improve the process of self-filling the cartridge compared to processes in the known art. Ensuring the stopper remains inside the cartridge when self-filling the cartridge improves the handling compared to processes in the known art. More specifically, a movement of the stopper may be restricted such that the stopper remains inside the cartridge when self-filling the cartridge. Thereby, the disclosed devices and methods may prevent a leakage of the fluid from the cartridge, for example, a leakage of the insulin from the cartridge. In particular, the disclosed devices may prevent the stopper from being accidentally removed from the cartridge.

The disclosed devices and methods may further improve the reliability of the process of self-filling a cartridge. A user may, for example, only be able to terminate the self-filling of the cartridge after filling the cartridge with a predefined volume of the fluid, such as insulin. In particular, the self-filling of the cartridge may only be terminated after a predefined filling amount, such as, for example, after a filling quantity of 50% and/or 100% of the cartridge. Thereby, information on the exact filling quantity may be available. Specifically, the exact filling quantity may be available for a medication pump, e.g., an insulin pump, and no subjective evaluation and/or assessment of the filling quantity by the user may be necessary. Thus, the dispensing time of the insulin may be precisely calculated, thereby enabling the medication pump to warn a user reliably before the end of the medicine supply, specifically, for example, before the insulin supply within the cartridge is depleted.

Summarizing and without excluding further possible embodiments, the following embodiments may be envisaged:

Embodiment 1: A filling aid for self-filling at least one cartridge from a storage vessel comprising at least one housing configured for receiving the cartridge, at least one stopper interacting with the housing and configured for entering the cartridge, and at least one cannula configured for piercing a septum of the cartridge, wherein the housing is configured to be activated such that:
the stopper is maintained outside the cartridge prior to activation,
upon activation, the stopper is inserted into the cartridge, and
the septum is pierced by the cannula.

Embodiment 2: The filling aid according to the preceding embodiment, wherein the housing is configured such that the septum of the cartridge is pierced by the cannula while advancing the stopper inside the cartridge.

Embodiment 3: The filling aid according to any one of the preceding embodiments, wherein the housing is configured to be activated in a multiple-step activation, wherein a first activation comprises inserting the stopper into the cartridge and wherein a second activation comprises piercing the septum by the cannula.

Embodiment 4: The filling aid according to any one of the preceding embodiments, wherein, prior to activation, a first gap exists between the stopper and the cartridge, and a second gap exists between the cannula and the septum.

Embodiment 5: The filling aid according to any one of the preceding embodiments, wherein the housing comprises at least one fill level indicator for indicating a fill level of the cartridge.

Embodiment 6: The filling aid according to any one of the preceding embodiments, wherein the housing comprises at least two housing parts and at least one guiding device, wherein, by means of the guiding device, the at least two housing parts are movable with respect to each other, thereby activating the housing and initiating a filling of the cartridge.

Embodiment 7: The filling aid according to the preceding embodiment, wherein one of the housing parts comprises a handle piece, wherein the stopper is connected to the handle piece by means of a coupling.

Embodiment 8: The filling aid according to the preceding embodiment, wherein the coupling comprises a bayonet joint.

Embodiment 9: The filling aid according to the preceding embodiment, wherein the bayonet joint comprises at least one undercut, wherein the undercut is configured to increase a transmissible force between the stopper and the handle piece.

Embodiment 10

The filling aid according to any one of the two preceding embodiments, wherein the bayonet joint comprises at least one centering pin, wherein the centering pin is configured to restrict a movement of the stopper and the handle piece with respect to each other.

Embodiment 11: The filling aid according to any one of the four preceding embodiments, wherein the handle piece comprises at least one handling recess.

Embodiment 12: The filling aid according to any one of the five preceding embodiments, wherein the handle piece comprises at least a first part of the guiding device.

Embodiment 13: The filling aid according to any one of the eight preceding embodiments, wherein the handle piece comprises at least a first part of the fill level indicator.

Embodiment 14: The filling aid according to any one of the eight preceding embodiments, wherein one of the housing parts comprises a connection piece, wherein the connection piece is connected to the cannula.

Embodiment 15: The filling aid according to the preceding embodiment, wherein the connection piece comprises at least a second part of the guiding device.

Embodiment 16: The filling aid according to any one of the eleven preceding embodiments, wherein the connection piece comprises at least a second part of the fill level indicator.

Embodiment 17: The filling aid according to any one of the three preceding embodiments, wherein the cannula is arranged inside the connection piece.

Embodiment 18: The filling aid according to any one of the four preceding embodiments, wherein the connection piece comprises at least one finger grip recess.

Embodiment 19: The filling aid according to any one of the five preceding embodiments, wherein the connection piece comprises at least one cartridge receptacle configured to receive the cartridge.

Embodiment 20: The filling aid according to any one of the six preceding embodiments, wherein the connection piece comprises at least one storage vessel receptacle configured to receive a storage vessel.

Embodiment 21: The filling aid according to the preceding embodiment, wherein the cannula is configured to pierce a seal of the storage vessel and to allow a transfer of a fluid between the storage vessel and the cartridge.

Embodiment 22: The filling aid according to the preceding embodiment, wherein the cannula has two opposing ends, each end having a sharp, a first end thereof being configured for piercing the septum of the cartridge and the second end thereof being configured for piercing the seal of the storage vessel.

Embodiment 23: The filling aid according to any one of the seventeen preceding embodiments, wherein the guiding device is configured to determine a relative positioning of at least two parts of the filling aid.

Embodiment 24: The filling aid according to any one of the preceding embodiments, wherein the housing comprises at least two abutments, wherein the cartridge is receivable in the housing such that the cartridge is fixed in between the two abutments.

Embodiment 25: A kit for self-filling at least one cartridge from a storage vessel, comprising at least one filling aid according to any one of the preceding embodiments, the kit further comprising at least one cartridge for receiving a fluid and receivable within the filling aid, the cartridge having at least one first opening covered by a septum and at least one second opening through which the stopper of the filling aid is insertable into the cartridge.

Embodiment 26: The kit according to the preceding embodiment, the kit further comprising at least one storage vessel filled with at least one fluid.

Embodiment 27: A use of the filling aid according to any one of the preceding embodiments referring to a filling aid for self-filling a cartridge for insulin delivery, specifically for use with a medication pump.

Embodiment 28: A method of manufacturing a filling aid for self-fillable cartridges, the method comprising:
 i) providing at least one housing for receiving the cartridge;
 ii) providing at least one stopper, wherein the stopper interacts with the housing, wherein the stopper is configured for entering the cartridge;
 iii) providing at least one cannula, wherein the cannula is configured for piercing a septum of the cartridge; and
 iv) maintaining the stopper outside of the cartridge, wherein the stopper is arranged such that, upon activation of the housing, the stopper can be inserted into the cartridge.

Embodiment 29: The method of manufacturing a filling aid for self-fillable cartridges according to the preceding embodiment, wherein the method further comprises:
 v) positioning the filling aid inside a permeable foil; and
 vi) sterilizing the filling aid in a sterilization process.

Embodiment 30: The method of manufacturing a filling aid for self-fillable cartridges according to any one of the two preceding embodiments, wherein the filling aid is a filling aid according to any one of the preceding embodiments referring to a filling aid.

Embodiment 31: A method of manufacturing a kit for self-fillable cartridges, the method comprising:
I) providing at least one cartridge for receiving a fluid;
II) providing at least one housing for receiving the cartridge;
III) providing at least one stopper, wherein stopper interacts with the housing, wherein the stopper is configured for entering the cartridge;
IV) providing at least one cannula, wherein the cannula is configured for piercing a septum of the cartridge; and
V) maintaining the stopper outside of the cartridge, wherein the stopper is arranged such that, upon activation of the housing, the stopper can be inserted into the cartridge;

Embodiment 32: The method of manufacturing a kit for self-fillable cartridges according to the preceding embodiment, wherein the method further comprises:
VI) positioning the filling aid inside a permeable foil; and
VII) sterilizing the filling aid in a sterilization process.

Embodiment 33: The method of manufacturing a kit for self-fillable cartridges according to any one of the two preceding embodiments, wherein the method comprises providing a storage vessel filled with at least one fluid.

Embodiment 34: The method of manufacturing a kit for self-fillable cartridges according to any one of the three preceding embodiments, wherein the kit is a kit according to any one of the preceding embodiments referring to a kit.

Embodiment 35: A method of using a filling aid for self-filling at least one cartridge from a storage vessel, the method comprising the following steps:
a) providing at least one housing for receiving the cartridge;
b) providing at least one stopper, wherein the stopper interacts with the housing, wherein the stopper is configured for entering the cartridge;
c) providing at least one cannula, wherein the cannula is configured for piercing a septum of the cartridge;
d) maintaining the stopper outside of the cartridge, wherein the stopper is arranged such that, upon activation of the housing, the stopper can be inserted into the cartridge; and
e) activating the housing, wherein the stopper is inserted into the cartridge and the septum is pierced by the cannula.

Embodiment 36: The method of using a filling aid according to the preceding embodiment, wherein the method further comprises maintaining the cannula outside of the septum prior to the activation of the housing.

Embodiment 37: The method of using a filling aid according to any one of the two preceding embodiments, wherein step e) of the method further comprises the following substeps:
e1) advancing the stopper inside the cartridge;
e2) mating the filling aid and a storage vessel;
e3) piercing a seal of the storage vessel; and
e4) transferring at least one fluid between the storage vessel and the cartridge through the cannula.

Embodiment 38: The method of using a filling aid according to any one of the three preceding embodiments, wherein piercing the septum by the cannula is performed while performing step e1) advancing the stopper inside the cartridge.

Embodiment 39: The method of using a filling aid according to any one of the four preceding embodiments, wherein the filling aid is a filling aid according to any one of the preceding embodiments referring to a filling aid.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein:

FIG. 6A shows an enlargement of a part of an embodiment of a handle piece in a perspective view;

FIGS. 6B and 6C show two perspective views of an embodiment of a stopper;

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
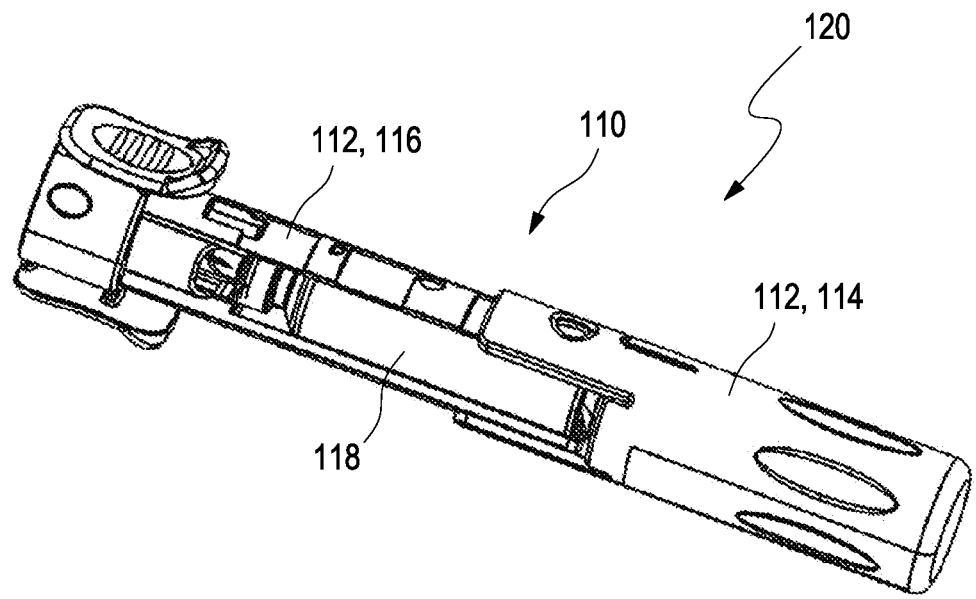
FIG. 1 shows a perspective view of an embodiment of a kit for self-filling at least one cartridge from a storage vessel comprising an embodiment of a filling aid and a cartridge.

FIG. 1 shows an embodiment of a filling aid 110 in a perspective view. The filling aid comprises a housing 112, wherein the housing 112 may include two housing parts. The first housing part may comprise a handle piece 114 and the second housing part may comprise a connection piece 116. The housing 112 is configured to be activated. However, in FIG. 1 the filling aid 110 is shown in a state prior to activation. The housing 112 is further configured for receiving a cartridge 118. Thus, the cartridge 118 is receivable within the filling aid 110 as shown in FIG. 1. A kit 120 for self-filling the at least one cartridge 118 is comprised of the filling aid 110 and the cartridge 118.

Figure 2:
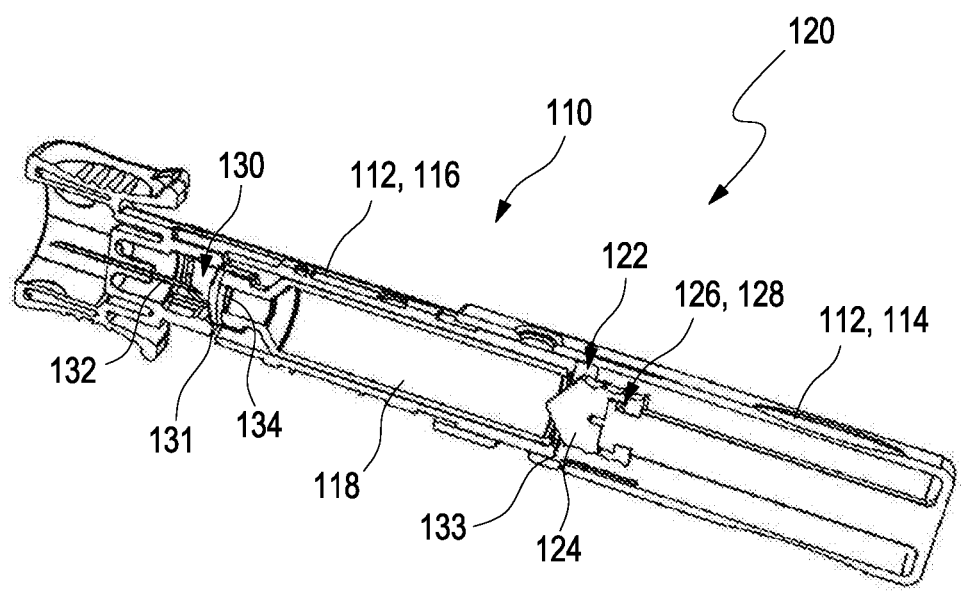
FIG. 2 shows a cross-sectional view of the embodiment of a kit comprising the embodiment of a filling aid and a cartridge shown in FIG. 1.

FIG. 2 shows a cross-sectional view of the embodiment of the kit 120, comprising the filling aid 110 and the cartridge 118, shown in FIG. 1. The filling aid 110 as shown in FIGS. 1 and 2 is in an initial state (also referred to as "initial position") prior to activation. In the initial state prior to activation, the housing 112 may be arranged such that a first gap 122 exists between a stopper 124, connected to the handle piece 114, and the cartridge 118. The stopper 124 interacts with the housing and is configured for entering the cartridge 118. The stopper 124 may further be connected to the handle piece 114 by means of a coupling 126, for example a bayonet joint 128. In the state prior to activation, the housing 112 may further be arranged such that a second gap 130 exists between a cannula 132 and a septum 134 of the cartridge 118. The cannula 132 may be connected to the connection piece 116. As can be seen in FIG. 2, the cannula 132 may be arranged inside the connection piece 116. Furthermore, the cannula 132 is configured for piercing the septum 134 of the cartridge 118. The housing may further comprise at least a first abutment 131 and a second abutment 133. In the state prior to activation, the cartridge 118 may be fixed between the first abutment 131 and the second abutment 133.

Figure 3:
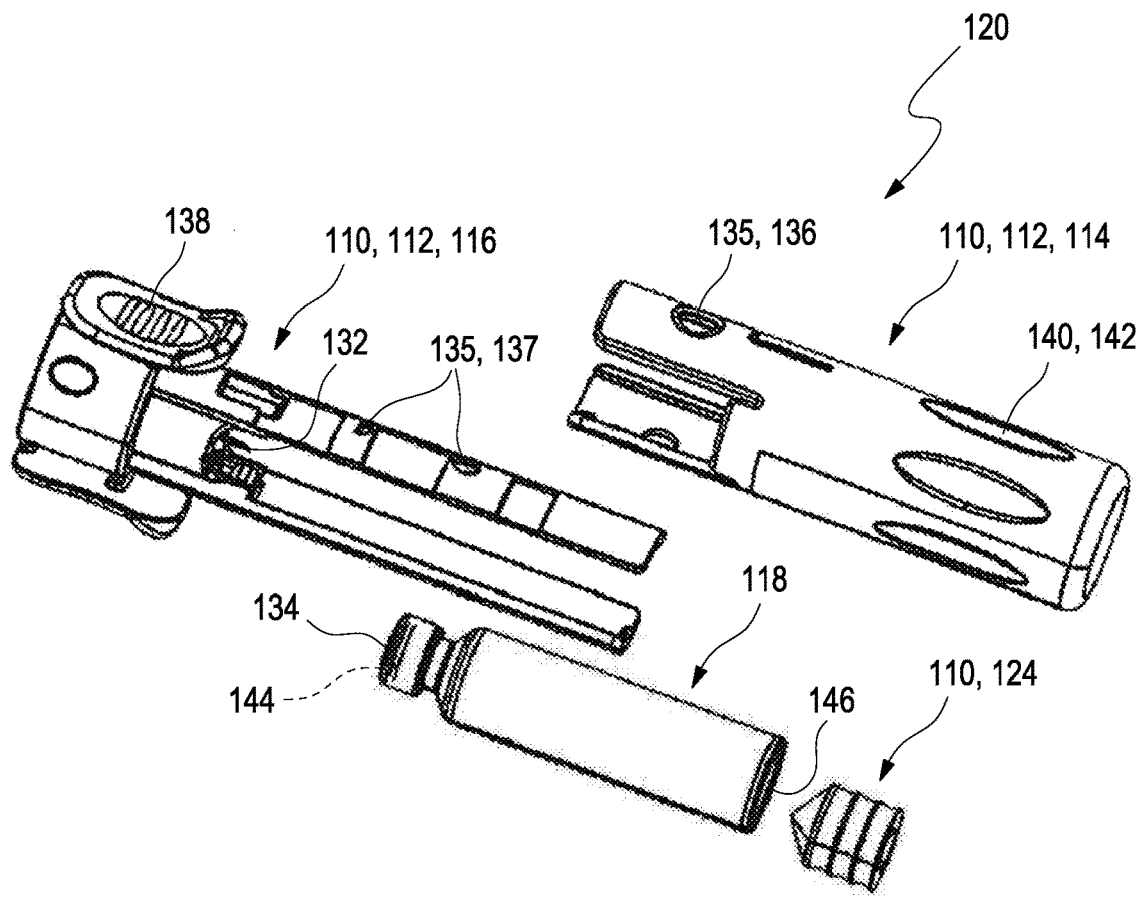
FIG. 3 shows an exploded view of the embodiment of a kit comprising an embodiment of a filling aid and a cartridge.

In FIG. 3 an exploded view of the embodiment of the kit 120, comprising an embodiment of the filling aid 110 and the cartridge 118, is shown. The cartridge 118, the handle piece 114, the connection piece 116 and the stopper 124 are displayed separately to allow a view of each of the components of the kit 120. Thus, the arrangement of the cartridge 118, the handle piece 114, the connection piece 116 and the stopper 124 to one another as shown in FIG. 3 is not intended to reveal information about the interaction of the components with one another.

The filling aid 110 comprises the housing 112, the stopper 124 and the cannula 132. The housing 112 may comprise the handle piece 114, the connection piece 116 and a fill level indicator 135. The fill level indicator 135 may be configured to indicate a fill level of the cartridge 118. The fill level indicator 135 may comprise a first part, specifically a fill level identifier 136 such as a vision panel shown in FIG. 3. The fill level indicator 135 may further comprise a second part, specifically a fill level indicator marking 137, such as a scale marking various fill levels. For example the scale may indicate two different fill levels as shown in FIG. 3, wherein the two markings indicate a fill level of 50% and a fill level of 100%. The fill level indicator 135 may be formed, in conjunction, by the fill level identifier 136, comprised by the handle piece 114, and the fill level indicator marking 137, comprised by the connection piece 116.

The connection piece 116 is connected to the cannula 132, such that the cannula 132 may be arranged inside the connection piece 116. The connection piece 116 may further comprise a finger grip recess 138. The finger grip recess 138 may be configured for defining a force transmission point. Specifically, the finger grip recess 138 may be configured to provide a defined space for placing at least one finger. For example, the finger grip recess 138 may provide a defined space for a user to hold the filling aid 110, specifically the connection piece 116, with two fingers, thereby allowing a user to transmit a force onto the connection piece 116. The finger grip recess 138 may comprise a grooved surface configured to increase a friction and/or grip between the finger and the connection piece 116 when applying a force onto the connection piece 116. The finger grip recess 138 may further have a curved shape configured to prevent slippage, specifically to prevent the finger from slipping off from the finger grip recess 138 when applying a force onto the connection piece 116. The force may specifically be applied onto the connection piece 114 when activating the housing 112.

The handle piece 114 may further comprise a handling recess 140. The handling recess may be configured to define a force transmission area for transmission of a force onto the handling piece 114. The handling recess 140 may comprise at least one opening 142. The opening 142 may have an oval shape as shown in FIG. 3. Other shapes of the opening 142 are also feasible. The opening 142 may be configured to increase friction and prevent slippage between a holder, for example a finger or a palm of a hand of the user, and the handle piece 114. Specifically the handling recess 140 may be configured to establish a grip when applying force onto the handling piece 114. The force may specifically be applied onto the handle piece 116 when activating the housing 112.

The cartridge 118 may have a cylindrical shape and two openings on each end of the cylinder. Specifically the cartridge may have a bottle shape with a bottle opening 144 at the top and a base opening 146 at the base of the bottle. The cartridge may comprise the septum 134, configured to seal the bottle opening 144. The stopper 124 may be configured to seal the base opening 146 of the cartridge 118.

Figure 4:
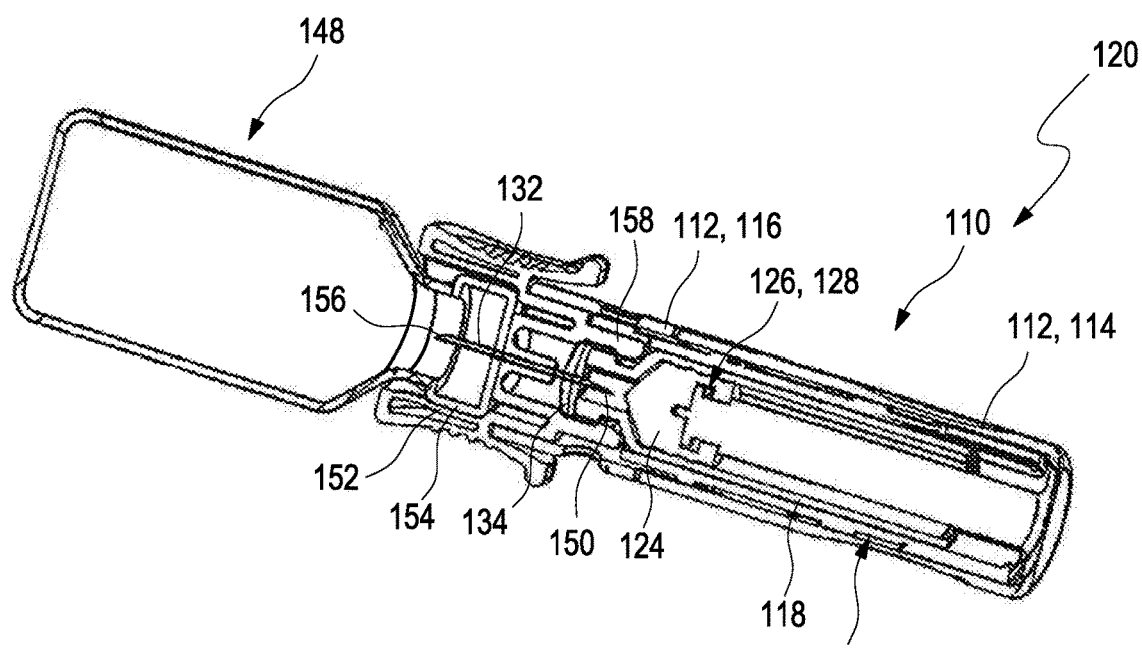
FIG. 4 shows a cross-sectional view of the embodiment of a filling aid, a cartridge and a storage vessel.

In FIG. 4 a cross-sectional view of the embodiment of a filling aid 110, a cartridge 118 and a storage vessel 148 is shown. Therein, the filling aid 110 is shown in an activated state. In the activated state (also referred to herein as "activated position"), the stopper 124 is located inside the cartridge 118 and the septum 134 is pierced by the cannula 132. Thereby, the septum 134 may be pierced by a first end of the cannula 132, wherein the first end comprises a first sharp 150. The cannula 132 may be configured to establish a fluidic connection between the storage vessel 148 and the cartridge 118. In the state of activation shown in FIG. 4, the storage vessel 148 is received in a storage vessel receptacle 152 formed by the connection piece 116. The storage vessel 148 may comprise a seal 154 configured for sealing the storage vessel 148. The seal 154 may be pierced by the cannula 132 to allow a transfer of a fluid between the storage vessel 148 and the cartridge 118. The seal 154 may be pierced by a second end of the cannula 132 opposing the first end of the cannula 132 comprising a second sharp 156. In the displayed state of activation, the cartridge 118 is received in a cartridge receptacle 158 comprised by the connection piece 116. The stopper 124 is connected to the handle piece 114 by means of a bayonet joint 128. The handle piece 114 may move with respect to the connection piece 114, thereby moving the stopper 124 inside the cartridge 118. The movement of the stopper 124 inside the cartridge 118 may change the pressure inside the cartridge 118, thereby actuating the transfer of the fluid between the storage vessel 148 and the cartridge 118. The handle piece 114 and the connection piece 116 may be movable toward and away from each other by means of a guiding device 160 illustrated in FIG. 4.

The guiding device 160 may be comprised by the housing 112. Further, the handle piece 114 and the connection piece 116 comprised by the housing 112 may be movable with respect to each other by means of the guiding device 160. The movement of the handle piece 114 and the connection piece 116 relative to each other may be activating the housing. The activation of the housing 112 may initiate a filling of the cartridge 118. Specifically, the movement of the handle piece 114 and the connection piece 116 relative to each other by means of the guiding device 160 may arrange the stopper 124 and/or the cartridge 118 and/or the cannula 132 in such a way that a filling of the cartridge 118 may be initiated. Preferably the movement of the at least two housing parts may activate the housing 112, such that an interaction between the stopper 124 and/or the cartridge 118 and/or the cannula 132 may be allowed.

Figure 5:
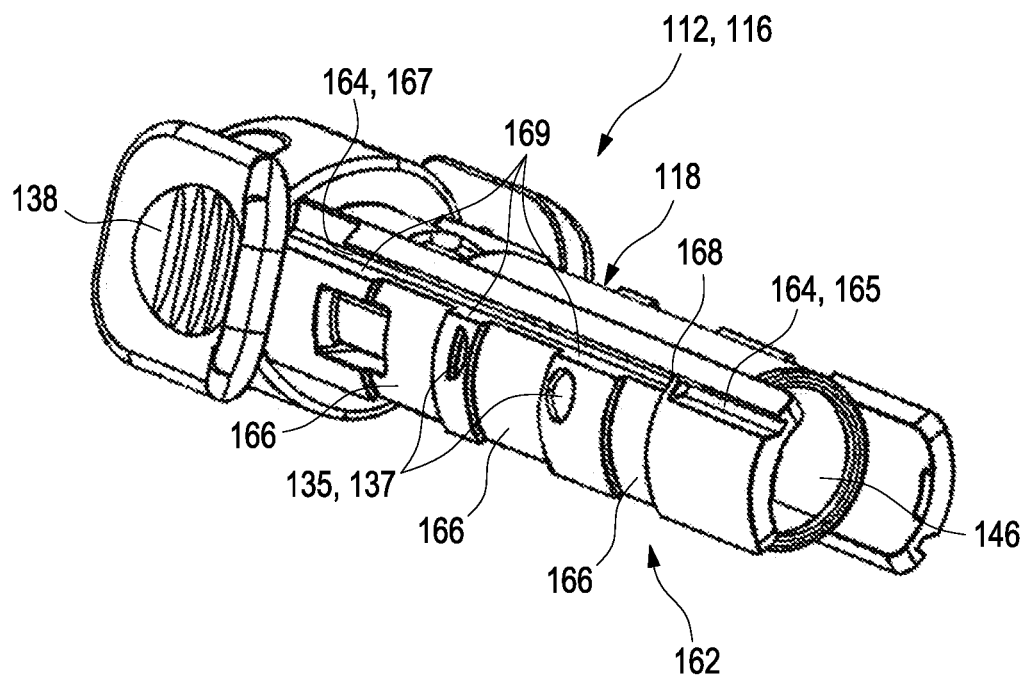
FIGS. 5A and 5B show perspective views of an embodiment of a second part of a housing and a cartridge (FIG. 5 A) and an embodiment of a first part of a housing (FIG. 5 B)
Figure 5:
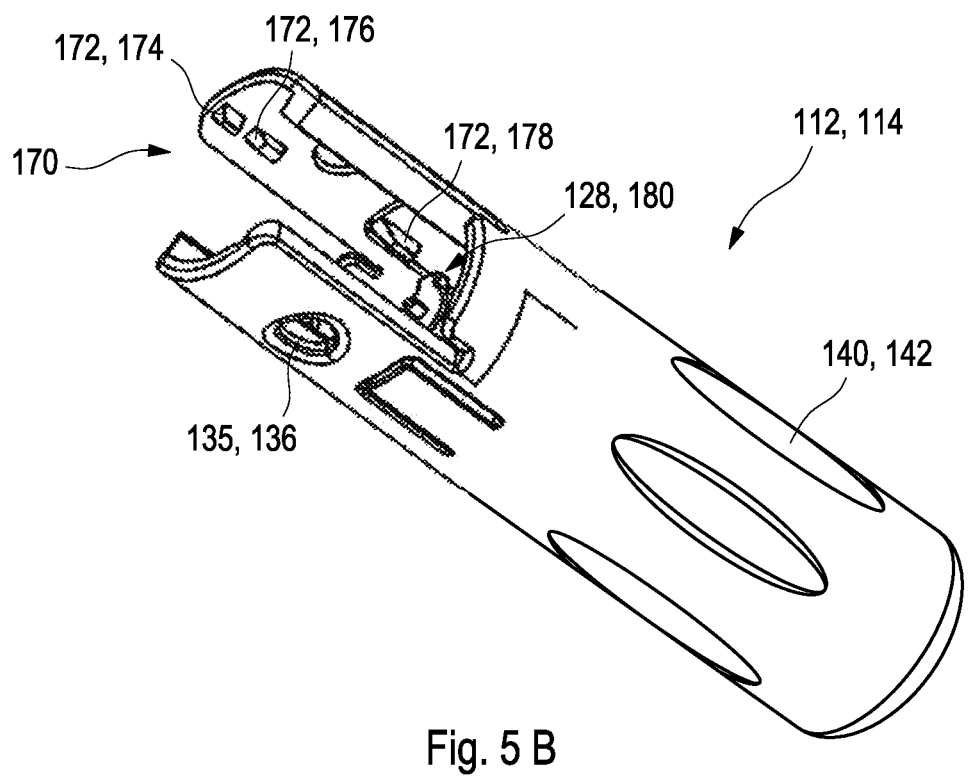

The guiding device 160 may comprise at least two separate parts. A first part of the guiding device may be configured for providing a trajectory 162, specifically by comprising means for defining a direction of movement, such as, for example, by comprising at least one groove 164 and/or at least one slot 166. In FIG. 5A an embodiment of a connection piece 116 comprising the first part of the guiding device 160 providing the trajectory 162 is shown in a perspective view. FIG. 5A further shows the cartridge 118 received in the connection piece 116. The groove 164 may be interrupted by a barrier 168. The barrier 168 may be configured for interrupting the groove 164. Thereby the barrier 168 may separate a first part of the groove 165 from a second part of the groove 167. The barrier 168 may further constrict a movement of a second part of the guiding device 160 configured to follow the trajectory 162. The second part of the guiding device 160 may specifically be a trailing structure 170. Thus, the barrier 168 may be configured to restrict a movement of the trailing structure 170 shown in FIG. 5B. The groove 164 may further be connected to at least one slot 166. Specifically one end of the slot 166 may merge into one edge of the groove 164. More specifically the at least one slot 166 may intersect the at least one edge of the groove 164. In particular, a plurality of slots 166 may intersect at least one edge of the groove 164. More particular, as shown in FIG. 5A, three slots 166 may intersect a first edge 169 of the groove 164.

In FIG. 5B an embodiment of a handle piece 114 is shown in a perspective view. The handle piece 114 comprises the trailing structure 170 configured for following the trajectory 162 shown in FIG. 5A. The trailing structure 170 may comprise at least one protrusion element 172. The protrusion element 172 may comprise a form configured to support a specific function, such as, for example, allowing a movement in one direction and restricting a reverse movement. For example, the protrusion element 172 may have the form of a wedge. A beveled edge of the wedge may allow a movement of the protrusion element over an obstacle in one direction, wherein a vertically falling edge opposing the beveled edge may prevent a reverse movement of the protrusion element. The trailing structure 170 may comprise a plurality of protrusion elements 172, specifically three protrusion elements 172 as shown in FIG. 5B. The plurality of protrusion elements 172 may differ in their form. Particularly, the form of a first protrusion element 174 may differ from a form of the second protrusion element 176 and/or from a form of a third protrusion element 178.

FIG. 6A shows an enlargement of a part of an embodiment of the handle piece 114 in a perspective view. The handle piece 114 may comprise a part of a bayonet joint 128 configured for establishing a releasable mechanical connection between the handle piece 114 and a stopper 124. An embodiment of the stopper 124 can be seen in FIG. 6B. The stopper 124 also comprising a part of the bayonet joint 128 configured for connecting the stopper 124 and the handle piece 114. Specifically, the handle piece 114 shown in FIG. 6A may comprise a first contour 180 of the bayonet joint 128, wherein the stopper shown in FIG. 6B 124 may comprise a second contour 182 of the bayonet joint 128. The first contour 180 and the second contour 182 may be configured for interacting with each other in a complementary fashion, thereby forming a bayonet joint 128. Thus, the first contour 180 may be a male bayonet contour comprising a protrusion. In a complementary fashion, the second contour 182 may be a female bayonet contour comprising a bayonet groove in which the protrusion of the first contour 180 may be guided. The first contour 180 may comprise at least one undercut 184. Particularly, the first contour 180 may comprise a plurality of undercuts 184, more particularly, the first contour 180 may comprise two undercuts 184 as can be seen in FIG. 6A. The undercut 184 may be configured to increase a transmissible tensile force of the bayonet joint 128, specifically a transmissible tensile force between the stopper 124 and the handle piece 114. The undercut 184 may have a jagged and/or tooth shaped form. The undercut 184 may be configured to get caught in the second contour 182 of the stopper 124 when the tensile force is applied. Specifically, by way of the applied tensile force, the undercut 184 may be configured to dig into and/or to get hooked in the surface of the stopper 124, thereby temporarily locking the bayonet joint 128. The temporary locking of the bayonet joint 128 may connect the handle piece 114 to the stopper 124 even when the second contour 182 of the stopper 124 is deformed by the strength of the tensile force. The undercut 184 may reduce a force transmitting area 186 within the bayonet joint 128. The undercut 184 may further relocate the force transmitting area 186 away from a first section edge 188 of the second contour 182 of the stopper 124 to a second section edge 190. An interconnection of the stopper 124 and the handle piece 114 may be formed by a sequence of movements or relative movements of the stopper 124 and the handle piece 114. The interconnection may be formed by a combination of a linear movement along an axis 192 and, subsequently, a clockwise rotational movement 194 around the axis 192 of the handle piece 114 with respect to the stopper 124 indicated by an arrow in the FIGS. 6A, 6B and 6C. The linear movement of the handle piece 114 inside the stopper 124 may be performed along the first section edge 188 of the second contour 182 of the stopper 124. Subsequently, the clockwise rotational movement 194 of the handle piece 114 with respect to the stopper 124 may be performed until a flank 196 of the first contour 180 comprised by the handle piece 114 physically contacts the second section edge 190 of the stopper 124.

The bayonet joint 128 may further comprise a centering pin 198. The centering pin 198 may be configured for restricting a relative movement of the stopper 124 and the handle piece 114, such as a movement initiated by vibrations occurring during transport and/or storing of the filling aid. The centering pin 198 may limit the relative movement of the stopper 124 and the handle piece 114 to the linear movement along the axis 192, the clockwise rotational movement 194 and reversible movements thereof.

FIG. 6C shows a perspective view of an embodiment of the stopper 124 shown in FIG. 6B from a different angle. The stopper 124 may comprise a conical part 200 having a conical shape. The stopper 124 may further comprise a cylindrical part 202 having an overall shape of a cylinder with varying diameters. The varying diameters of the cylindrical part 202 may create a shell surface with a wavelike structure. The wavelike structure may be configured to reduce friction between the surface of the stopper 124 and an inner surface of a cartridge 118. The conical part 200 of the stopper 124 may directly merge into the cylindrical part 202 of the stopper 124.

Figure 7:
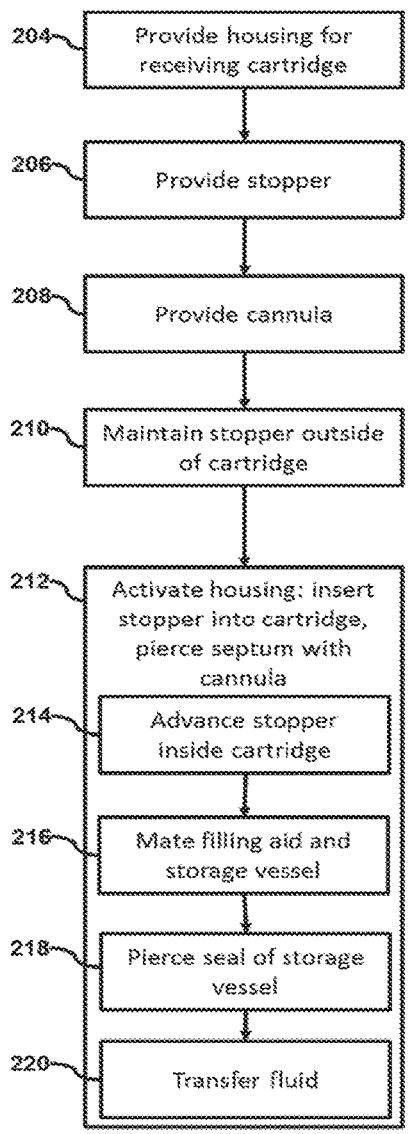
FIG. 7 shows a flow chart of a method of using a filling aid for self-filling at least one cartridge from a storage vessel.

In FIG. 7 a flow chart of a method of using a filling aid 110 for self-filling at least one cartridge 118 from a storage vessel 148 is shown. The method may comprise a plurality of steps. The method steps may be performed in the given order. However, other orders of the method steps are feasible. Further, one or more of the method steps may be performed in parallel and/or on a timely overlapping fashion. Further, one or more of the method steps may be performed repeatedly. Further, additional method steps may be present which are not listed. The method comprises a first step a) (method step 204) providing at least one housing 112 for receiving the cartridge 118. The housing 112 may specifically comprise a handle piece 114 and a connection piece 116. The method further comprises a second step b) (method step 206) providing at least one stopper 124, wherein the stopper 124 interacts with the housing 112, wherein the stopper 124 is configured for entering the cartridge 118. Further, the method comprises a third step c) (method step 208) providing at least one cannula 132, wherein the cannula 132 is configured for piercing a septum 134 of the cartridge 118.

The method of using the filling aid 110 for self-filling the at least one cartridge 118 from the storage vessel 148 further comprises step d) (method step 210) maintaining the stopper 124 outside of the cartridge 118, wherein the stopper 124 is arranged such that, upon activation of the housing 112, the stopper 124 can be inserted into the cartridge 118. Specifically, as illustrated in FIG. 2, the stopper 124 may be maintained outside of the cartridge 118, such that a first gap 122 exists between the stopper 124 and the cartridge 118. Further, a second gap 130 may exist between the cannula 132 and the septum 134 of the cartridge 118.

Further, the method of using the filling aid 110 for self-filling the at least one cartridge 118 from the storage vessel 148 further comprises step e) (method step 212) activating the housing 112, wherein the stopper 124 is inserted into the cartridge 118 and the septum 134 is pierced by the cannula 132. The housing 112 may comprise the connection piece 116 and the handle piece 114. In particular, the housing 112 may be activated by moving the connection piece 116 and the handle piece 114 with respect to each other. The connection piece 116 and the handle piece 114 may be movable with respect to each other by means of a guiding device 160. The guiding device 160 may be formed by a first part of the guiding device 160 as shown in FIG. 5A and a second part of the guiding device 160 as shown in FIG. 5B, in conjunction. Thus, a trailing structure 170 comprised by the handle piece 114 may be configured to follow a trajectory 162 comprised by the connection piece 116. In a state prior to activation, at least one protrusion element 172 may be arranged in a first part of the groove 165. Specifically, another one of the protrusion elements 172 may be arranged in a second part of the groove 167, thereby securing the handle piece 114 to the connection piece 116 and vice versa. Particularly, a first protrusion element 174 may be arranged in the second part of the groove 167 and a second protrusion element 176 may be arranged in the first part of the groove 165. A third protrusion element 178 may be arranged outside of the groove 164 in the state prior to activation. A movement of the handle piece 114 respectively to the connection piece 116 may be activating the housing 112. In an initial movement the handle piece 114 and the connection piece 114 may be pushed together, thereby reducing the distance between the handle piece 114 and the connection piece 116. Thereby, the second protrusion element 172 may be pushed over the barrier 168. Thus, the second protrusion element 172 may be arranged in the second part of the groove 167. Sequentially, the third protrusion element 178 may also be pushed over the barrier 168, thereby being arranged in the second part of the groove 167.

Step e) (method step 212) may comprise a plurality of substeps, such as, for example, four substeps. A first substep e1) (method step 214) may comprise advancing the stopper 124 inside the cartridge 118. As the handle piece 114 and the connection piece 116 are pushed together, the stopper 124 is placed inside the cartridge 118 and the septum 134 of the cartridge 118 is pierced by the cannula 132, as illustrated in FIG. 4. The protrusion elements 172 may have a specific form, allowing a movement over the barrier 168 in one direction, wherein restricting a reverse movement. Thus, once the protrusion elements 172 comprised by the handle piece 114 are pushed over the barrier 164, a reverse movement may no longer be possible. An axial movement of the handle piece 114 with respect to the connection piece 116 may only be possible between a minimum and a maximum fill level of the cartridge 118. Therefore, the barrier 168 may prevent the stopper 124 from sliding out of the cartridge 118.

A second substep e2) (method step 216) may comprise mating the filling aid 110 and a storage vessel 148, and a third substep e3) (method step 218) may comprise piercing a seal 154 of the storage vessel 148. Specifically, the storage vessel 148 may be receivable within a storage vessel receptacle 152 comprised by the connection piece 116, as illustrated in FIG. 4. Particularly, the storage vessel 148 and the filling aid 110 may be mated by pushing the storage vessel 148 and the storage vessel receptacle 152 together, such that the storage vessel 148 may be received within the storage vessel receptacle 152. The connection piece 116 may further be connected to the cannula 132, such that, for example, when the storage vessel 148 is received within the storage vessel receptacle 152, the seal 154 of the storage vessel 148 may be pierced by the cannula 132.

A fourth substep e4) (method step 220) may comprise transferring at least one fluid between the storage vessel 148 and the cartridge 118 through the cannula 132. The cannula 132 may, specifically, connect the storage vessel 148 and the cartridge 118, as illustrated in FIG. 4. The connection between the storage vessel 148 and the cartridge 118 may particularly be a fluidic connection. Thus, the fluid, such as, for example, the insulin, may be transferred between the storage vessel 148 and the cartridge 118 through the cannula 132, e.g., by moving handle piece 114 away from connection piece 116. Specifically, the fluid may be transferred from the storage vessel 148 to the cartridge 118, thereby filling the cartridge with the fluid, e.g., the insulin.

Figure 8:
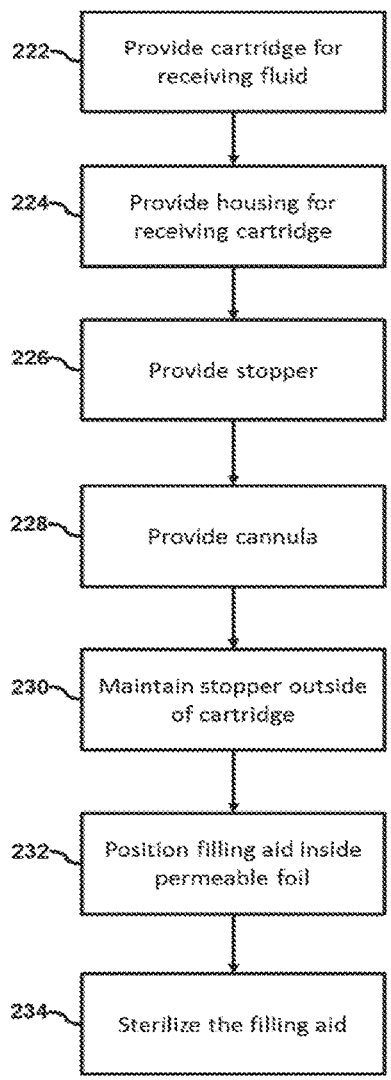
FIG. 8 shows a flow chart of a method of manufacturing a kit for self-fillable cartridges.

In FIG. 8, a flow chart of a method of manufacturing a kit 120 for self-fillable cartridges is shown. The method may comprise a plurality of steps. The method steps may be performed in the given order. However, other orders of the method steps are feasible. Further, one or more of the method steps may be performed in parallel and/or on a timely overlapping fashion. Further, one or more of the method steps may be performed repeatedly. Further, additional method steps may be present which are not listed. The method comprises step I) (method step 222) providing at least one cartridge 118 for receiving a fluid. Specifically, a cartridge 118 as illustrated in FIG. 1 may be provided.

The method of manufacturing the kit 120 further comprises step II) (method step 224) providing at least one housing 112 for receiving the cartridge 118. Specifically, the housing 112 as illustrated in FIGS. 1 and 2 may be provided. The method of manufacturing the kit 120 also comprises step III) (method step 226) providing at least one stopper 124, wherein stopper 124 interacts with the housing 112, wherein the stopper 124 is configured for entering the cartridge 118. Specifically, the stopper 124 as illustrated in FIGS. 2 and 3 may be provided. Further, the method for manufacturing the kit 120 comprises step IV) providing at least one cannula 132, wherein the cannula 132 is configured for piercing a septum 134 of the cartridge 118. Particularly, a cannula 132 as illustrated in FIG. 2 may be provided.

Further, the method of manufacturing the kit 120 comprises step V) (method step 230) maintaining the stopper 124 outside of the cartridge 118, wherein the stopper 124 is arranged such that, upon activation of the housing 112, the stopper can be inserted into the cartridge 118. Specifically, the stopper 124 may be maintained outside the cartridge 118, such that, for example a first gap exists between the stopper 124 and the cartridge 118, as illustrated in FIG. 2. Further, a second gap 130 may exist between the cannula 132 and the septum 134 of the cartridge 118.

The method of manufacturing the kit 120 may further comprise step VI) (method step 232) positioning the filling aid 110 inside a permeable foil, and step VII) (method step 234) sterilizing the filling aid 110 in a sterilization process. Specifically, the permeable foil may be configured for use within the sterilization process, such that a sterilizing agent, e.g., ethylene oxide, may be able to penetrate the permeable foil in the sterilization process. Particularly, the filling aid 110 may be sterilized by the sterilizing agent within the sterilization process.

Figure 9:
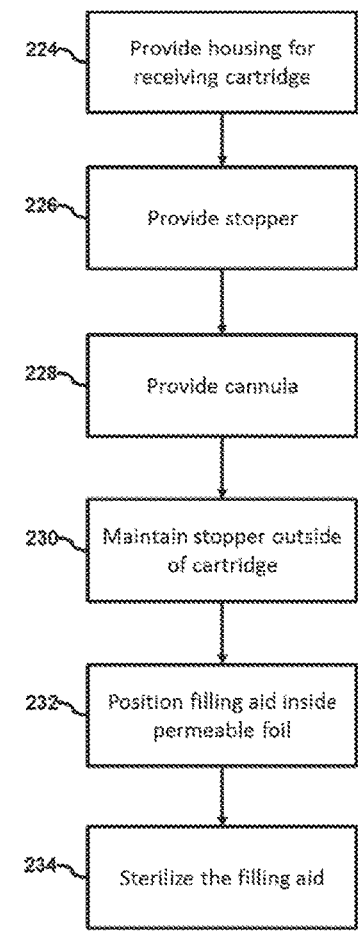
FIG. 9 shows a flow chart of a method of manufacturing a filling aid for self-fillable cartridges.

In FIG. 9, a flow chart of a method of manufacturing a filling aid 110 for self-finable cartridges is shown. The method may comprise a plurality of steps. The method steps may be performed in the given order. However, other orders of the method steps are feasible. Further, one or more of the method steps may be performed in parallel and/or on a timely overlapping fashion. Further, one or more of the method steps may be performed repeatedly. Further, additional method steps may be present which are not listed. The method of manufacturing the filling aid 110 for self-fillable cartridges 118 specifically comprises a plurality of steps that are also included in the method for manufacturing a kit 120 for self-fillable cartridges. Thus, reference may be made to the description given above. In particular, the steps II)-V) of the method of manufacturing the kit 120 for self-fillable cartridges equal the steps i)-iv) comprised by the method of manufacturing the filling aid 110 for self-fillable cartridges. The method of manufacturing the filling aid 110 for self-fillable cartridges may further comprise step v) positioning the filling aid inside a permeable foil, wherein step v) is equivalent to step VI). Further, the method of manufacturing the filling aid 110 may comprise step vi) sterilizing the filling aid in a sterilization process, wherein step vi) equals step VII).

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS 110 filling aid
112 housing
114 handle piece
116 connection piece
118 cartridge
120 kit
122 first gap
124 stopper
126 coupling
128 bayonet joint
130 second gap
131 first abutment
132 cannula
133 second abutment
134 septum
135 fill level indicator
136 fill level identifier
137 fill level indicator marking
138 finger grip recess
140 handling recess
142 opening
144 bottle opening
146 base opening
148 storage vessel
150 first sharp
152 storage vessel receptacle
154 seal
156 second sharp
158 cartridge receptacle
160 guiding device
162 trajectory
164 groove
165 first part of the groove
166 slot
167 second part of the groove
168 barrier
169 first edge of the groove
170 trailing structure
172 protrusion element
174 first protrusion element
176 second protrusion element
178 third protrusion element
180 first contour
182 second contour
184 undercut
186 force transmitting area
188 first section edge
190 second section edge
192 axis
194 clockwise rotational movement
196 flank
198 centering pin
200 conical part
202 cylindrical part
204 step a): providing at least one housing for receiving the cartridge
206 step b): providing at least one stopper, wherein the stopper interacts with the housing, wherein the stopper is configured for entering the cartridge
208 step c): providing at least one cannula, wherein the cannula is configured for piercing a septum of the cartridge
210 step d): maintaining the stopper outside of the cartridge, wherein the stopper is arranged such that, upon activation of the housing, the stopper can be inserted into the cartridge
212 step e): activating the housing, wherein the stopper is inserted into the cartridge and the septum is pierced by the cannula
214 substep e1): advancing the stopper inside the cartridge
216 substep e2): mating the filling aid and a storage vessel
218 substep e3): piercing a seal of the storage vessel
220 substep e4): transferring at least one fluid between the storage vessel and the cartridge through the cannula
222 step I): providing at least one cartridge for receiving a fluid
224 step II) and i): providing at least one housing for receiving the cartridge
226 step III) and ii): providing at least one stopper
228 step IV) and iii): providing at least one cannula
230 step V) and iv): maintaining the stopper outside of the cartridge, wherein the stopper is arranged such that, upon activation of the housing, the stopper can be inserted into the cartridge
232 step VI): positioning the filling aid inside a permeable foil
234 step VII): sterilizing the filling aid in a sterilization process

What is claimed is:

1. A filling aid for self-filling a cartridge from a storage vessel, the filling aid comprising:
    a housing configured to receive the cartridge;
    a stopper that interacts with the housing and is configured to enter the cartridge; and
    a cannula configured to pierce a septum of the cartridge;
    wherein the housing is movable from an initial position in which the stopper is maintained outside the cartridge to an activated position in which the stopper is inserted in the cartridge and the septum is pierced by the cannula.

2. The filling aid according to claim 1, wherein, during movement of the housing from the initial position to the activated position, the cartridge is pierced by the cannula and the stopper is advanced inside the cartridge.

3. The filling aid according to claim 1, wherein, in the initial position, a first gap exists between the stopper and the cartridge and a second gap exists between the cannula and the septum.

4. The filling aid according to claim 1, wherein the housing comprises a fill level indicator for indicating a fill level of the cartridge.

5. The filling aid according to claim 1, wherein the housing comprises two housing parts and a guide that guides the movement of the two housing parts with respect to each other from the initial position to the activated position.

6. The filling aid according to claim 5, wherein one of the housing parts comprises a handle piece and a coupling connecting the stopper to the handle piece.

7. The filling aid according to claim 5, wherein one of the housing parts comprises a connection piece connected to the cannula.

8. The filling aid according to claim 7, wherein the connection piece comprises a cartridge receptacle configured to receive the cartridge.

9. The filling aid according to claim 7, wherein the connection piece comprises a storage vessel receptacle configured to receive a storage vessel.

10. A kit for self-filling at least one cartridge from a storage vessel, comprising:
    a filling aid according to claim 1;
    a cartridge for receiving a fluid and configured to be received within the filling aid, the cartridge having a first opening covered by a septum and a second opening through which the stopper of the filling aid is insertable into the cartridge.

11. A method of manufacturing a filling aid for a self-fillable cartridge, the method comprising:
    i) providing a housing for receiving the cartridge;
    ii) providing a stopper configured to interact with the housing, the stopper being configured to enter the cartridge;
    iii) providing a cannula configured for piercing a septum of the cartridge; and
    iv) maintaining the stopper outside of the cartridge, wherein the stopper is arranged such that, upon activation of the housing, the stopper is inserted into the cartridge.

12. The method of manufacturing of claim 11, comprising providing a cartridge for receiving a fluid.

13. A method of using a filling aid for self-filling a cartridge from a storage vessel, the method comprising:
    a) providing a housing, a stopper and a cannula;
    b) placing the cartridge in the housing in an initial position of the housing in which the stopper is maintained outside the cartridge; and
    c) moving the housing to an activated position during which the stopper is inserted in the cartridge and the septum is pierced by the cannula.

14. The method of claim 13, wherein the cannula is maintained outside of the septum prior to the moving of the housing to the activated position.

15. The method of claim 13, wherein further comprising:
    mating the filling aid to a storage vessel;
    piercing a seal of the storage vessel; and
    transferring a fluid between the storage vessel and the cartridge through the cannula.

16. The filling aid according to claim 1, wherein, in the initial position, a first gap exists between the stopper and the cartridge.

17. The method of claim 11 wherein the step of maintaining the stopper outside of the cartridge includes forming a first gap between the stopper and the cartridge.

18. The method of claim 13 wherein the step of placing the cartridge in the housing in an initial position of the housing in which the stopper is maintained outside the cartridge includes forming a first gap between the stopper and the cartridge in the initial position of the housing.

* * * * *